(12) United States Patent
Amil Marletti et al.

(10) Patent No.: US 11,357,400 B2
(45) Date of Patent: Jun. 14, 2022

(54) IMAGE PROCESSING METHOD FOR GLAUCOMA DETECTION AND COMPUTER PROGRAM PRODUCTS THEREOF

(71) Applicants: UNIVERSITAT POLITECNICA DE CATALUNYA, Barcelona (ES); MAX-PLANCK-GESELLSCHAFT ZUR FÖRDERUNG DER WISSENSCHAFTEN E.V., Munich (DE)

(72) Inventors: Pablo Amil Marletti, Terrassa (ES); Cristina Masoller, Terrassa (ES); Elena Arrondo Murillo, Barcelona (ES); Ulrich Parlitz, Gleichen (DE); Cecilia Salinas Almela, Barcelona (ES)

( * ) Notice: Subject to any disclaimer, the term of this patent is extended or adjusted under 35 U.S.C. 154(b) by 189 days.

(21) Appl. No.: 16/772,097

(22) PCT Filed: Dec. 11, 2017

(86) PCT No.: PCT/IB2017/057792
§ 371 (c)(1),
(2) Date: Jun. 11, 2020

(87) PCT Pub. No.: WO2019/116074
PCT Pub. Date: Jun. 20, 2019

(65) Prior Publication Data
US 2020/0305706 A1    Oct. 1, 2020

(51) Int. Cl.
*A61B 3/10*    (2006.01)
*G06T 7/35*    (2017.01)
(Continued)

(52) U.S. Cl.
CPC ............ *A61B 3/102* (2013.01); *G06K 9/6276* (2013.01); *G06T 5/002* (2013.01); *G06T 7/0014* (2013.01);
(Continued)

(58) Field of Classification Search
CPC .......... A61B 3/102; G06T 2207/10101; G06T 2207/30041; G06T 7/0014; G06T 7/0012; G06T 7/35; G06T 5/002
See application file for complete search history.

(56) References Cited

U.S. PATENT DOCUMENTS

| | | | |
|---|---|---|---|
| 7,474,775 B2* | 1/2009 | Abramoff | G06T 7/0012 382/128 |
| 2009/0268159 A1* | 10/2009 | Xu | A61B 3/1233 351/246 |

(Continued)

OTHER PUBLICATIONS

Adam Switonski et al., Dimensionality Reduction of Multispectral Images Representing Anatomical Structures of an Eye, International Multi Conference of Engineers and Computer Science 2012, vol. I. Mar. 14-16, 2012, Hong Kong.

(Continued)

*Primary Examiner* — Gandhi Thirugnanam
(74) *Attorney, Agent, or Firm* — Eugenio J. Torres-Oyola; Victor M. Rodriguez-Reyes; Rafael Rodriguez-Muriel

(57) ABSTRACT

The method comprises storing a set of images captured of the anterior chamber of various eyes, and using a processor for: a) processing some of said stored images by implementing an homogenization process that adjusts an horizontal and a vertical spatial resolution of each image of the set to be the same, and a centering and aligning process that computes statistical properties of the images, and uses said computed statistical properties to compute a centroid and a covariance matrix of each image; b) performing pair-wise distance measures between images of said processed images providing a pair-wise distance matrix; c) analyzing said pair-wise distance matrix by executing a nonlinear dimensionality reduction algorithm that assigns a point in an n-dimensional space associated to each analyzed image; and d) outputting (Continued)

the results of said analysis in a visual way enabling being usable to detect if said eyes suffer from glaucoma.

16 Claims, 2 Drawing Sheets

(51) Int. Cl.
| | |
|---|---|
| *G16H 50/70* | (2018.01) |
| *G06K 9/62* | (2022.01) |
| *G06T 5/00* | (2006.01) |
| *G06T 7/00* | (2017.01) |

(52) U.S. Cl.
CPC .............. *G06T 7/35* (2017.01); *G16H 50/70* (2018.01); *G06T 2207/30041* (2013.01)

(56) References Cited

U.S. PATENT DOCUMENTS

| | | | | |
|---|---|---|---|---|
| 2010/0220914 A1* | 9/2010 | Iwase | ................... | G06T 7/0012 |
| | | | | 382/131 |
| 2014/0143251 A1* | 5/2014 | Wang | ................... | G06F 16/285 |
| | | | | 707/737 |
| 2014/0307958 A1* | 10/2014 | Wang | ................... | G06K 9/6256 |
| | | | | 382/159 |
| 2015/0380009 A1* | 12/2015 | Chang | ................... | G10L 13/00 |
| | | | | 704/263 |
| 2020/0305706 A1* | 10/2020 | Amil Marletti | ........ | A61B 3/102 |

OTHER PUBLICATIONS

Begona Acha et al., Burn Depth Analysis Using Multidimensional Scaling Applied to Psychophysical Experiment Data, pp. 1111-1120, IEE Transactions on Medical Imaging, vol. 32,, No. 6, Jun. 2013.

Frank Klawonn, et al., Case-Centered Multidimensional Scaling for Classification Visualisation in Medical Diagnosis, pp. 137-148, Springer-Verlag, Berlin Heidelberg 2013.

Calvin R. Maurer, et al., A Review of Medical Image Registration, Interactive Image-Guide Neurosurgery, Chapter 3, pp. 17-44.

Alireza Akhbardeh et al., Comparative Analysis of Nonlinear Dimensionality Reduction Techniques for Breast MRI segmentation, Med. Phys. 39 (4), Apr. 2012, pp. 2275-2289.

* cited by examiner

IMAGE PROCESSING METHOD FOR GLAUCOMA DETECTION AND COMPUTER PROGRAM PRODUCTS THEREOF

TECHNICAL FIELD

The present invention is directed, in general, to the field of imaging processing methods for detecting diseases. In particular, the invention relates to an image processing method and computer program products for glaucoma detection.

BACKGROUND OF THE INVENTION

Glaucoma is a major blinding eye disease that could be detected by processing images of the anterior chamber angle of an eye.

There are known some patent and patent applications in this field.

U.S. Pat. No. 9,579,016 B2 describes embodiments of optical coherence tomography (OCT) measurement and analysis techniques that enable precise 3D anterior chamber angle measurement from major, pertinent landmarks in the eye. Such techniques result in a more reliable, quantifiable angle measurement technique that is both non-invasive and non-contact in nature, thereby improving clinical practicality, while improving patient comfort and care. For example, a method is provided for in vivo imaging of an eye, including taking a plurality of OCT line scans of an eye to obtain a 3-dimensional (3D) radial scan pattern, the individual line scans including a plurality of axial scans, and obtaining a three-dimensional image of an anterior chamber angle of the eye from the radial scan pattern.

International patent application WO-A1-2016108755 discloses a method and apparatus for aligning a two-dimensional eye image with a predefined axis by rotation at a rotation angle. The method comprises deriving the rotation angle and a de-noised image, which minimizes a cost function comprising (i) a complexity measure of the de-noised image and (ii) magnitude of a noise image obtained by rotating the first image by the rotation angle and subtracting the de-noised image. Moreover, related methods and apparatus are disclosed for aligning a plurality of images with the predefined axis before alignments in transverse and parallel directions, as well as averaging the aligned images, in further embodiments, a method and apparatus of determining angle closure are disclosed, using a database of reference eye images with and without eye closure, the method comprising obtaining a two dimensional eye image, determining respective weights for each reference images that minimize a cost function comprising the difference between the received image and sum of the weighted reference images; identifying at least one of the first and second reference images having least differences with received image and determining whether the eye exhibits eye closure based on the received image being closer to first or second weighted reference images.

Patent application US-A1-2016228000 relates to a computer aided visualization and diagnosis by volume analysis of optical coherence tomography (OCT) angiographic data. In one embodiment, such analysis comprises acquiring an OCT dataset using a processor in conjunction with an imaging system; evaluating the dataset, with the processor, for flow information using amplitude or phase information; generating a matrix of voxel values, with the processor, representing flow occurring in vessels in the volume of tissue; performing volume rendering of these values, the volume rendering comprising deriving three dimensional position and vector information of the vessels with the processor; displaying the volume rendering information on a computer monitor; and assessing the vascularity, vascular density, and vascular flow parameters as derived from the volume rendered images.

International patent application WO-A1-2015130663 discloses systems and techniques for detecting glaucoma in a subject based on retinal vessel relief height obtained from optical coherence tomography (OCT) image data. In one example approach, a retinal vessel relief height relative to a retinal plane may be calculated from OCT image data and the presence or absence of a glaucoma condition may be determined based on the retinal vessel relief height.

U.S. Pat. No. 8,687,866 B2 discloses methods and systems for processing images of the anterior chamber angle of an eye. An optical coherence tomography (OCT) image of the anterior chamber of an eye is processed to determine automatically a location in the image corresponding to Schwalbe's line. First, the method finds the location of the corneal endothelium. Then the method fits a model to the detected corneal endothelium. Then the method determines the location of Schwalbe's line based on the relationship between the detected corneal endothelium and the fitted model, such as where the detected corneal endothelium diverges most from the fitted model. The Schwalbe's line is used to obtain a numerical measure of the anterior chamber angle of the eye. The method can be used in a process for screening patients for glaucoma. In the case of patients found to be suffering from glaucoma, treatment can be performed.

U.S. Pat. No. 9,357,911 B2 describes systems and methods for improving the reliability of glaucoma diagnosis and progression analysis. The measurements made from one type of diagnostic device are adjusted based on another measurement using a priori knowledge of the relationship between the two measurements including the relationship between structure and function, knowledge of disease progression, and knowledge of instrument performance at specific locations in the eye. The adjusted or fused measurement values can be displayed to the clinician, compared to normative data, or used as input in a machine learning classifier to enhance the diagnostic and progression analysis of the disease Finally, international patent application WO-A1-2017087018 relates to the field of clinical diagnosis and monitoring of ocular pathologies utilizing spectral domain optical coherence tomography (SD-OCT) and provides automated methods for segmenting and analyzing an OCT image and automated methods for diagnosing ocular pathology based thereon.

Moreover, scientific document 'Automatic Anterior Chamber Angle Assessment for HD-OCT Images' Jing Tian et. al. also discloses an algorithm which automatically detects a new landmark, Schwalbe's line, and measures the anterior chamber angle in high-definition OCT images for glaucoma detection. The distortion caused by refraction is corrected by dewarping the HD-OCT images, and three biometric measurements are defined to quantitatively assess the anterior chamber angle.

None of the prior art documents allow automatically ordering the images captured from the anterior chamber minimizing the amount of information needed. Therefore, new imaging processing methods are needed for glaucoma detection.

DESCRIPTION OF THE INVENTION

Embodiments of the present invention provides, according to one aspect, an image processing method for glaucoma detection, the method comprising storing in a database (or in a memory) a set of images captured of the anterior chamber of various eyes and using at least one processor to perform the following steps:

a) processing (some or all) of said stored images by implementing an homogenization process that at least adjusts an horizontal and a vertical spatial resolution of each image of the set to be the same, and a centering and aligning process that computes statistical properties of the images, and uses said computed statistical properties to compute a centroid and a covariance matrix of each image;
   b) performing pair-wise distance measures between images of said processed images providing a pair-wise distance matrix;
   c) analyzing said pair-wise distance matrix by executing a first nonlinear dimensionality reduction algorithm such as the IsoMap algorithm or a t-SNE algorithm, among others, that assigns a point in an n-dimensional space associated to each analyzed image; and
   d) outputting the results of said analysis in a visual way enabling being usable to detect if the eyes suffer from glaucoma.

According to a preferred embodiment, the set of images of the anterior chamber are optical coherence tomography (OCT) images.

In an embodiment, the above-mentioned homogenization process further converts the intensity of each pixel of each image to a double-precision floating-point number representation. In addition, said step a) may further implement a filtering process (after the homogenization process) that applies a two-dimensional rectangular median filter or an anisotropic diffusion filter to each image, or both. Instead of previous filtering processes other could also be used for instance a bilateral filter, a guide filter, a total variation denoising, a convolutional (Gaussian) filter, a non-local means filtering, or combinations thereof.

In an embodiment, said step c), besides executing the first nonlinear dimensionality reduction algorithm, further executes a community detection algorithm to an adjacency matrix derived from the pair-wise distance matrix to identify clusters or groups of similar images. Preferably, the community detection algorithm comprises an InfoMap algorithm. However, any of the following algorithms could also be used: the DBSCAN algorithm, the Leading eigenvector algorithm, the Fast Greedy Modularity Maximization algorithm, the Walktrap algorithm, the Label Propagation algorithm, the Spinglass algorithm, or the Edge Betweeness algorithm.

The outputting of the results may be done in different ways. In a first embodiment, and considering that in said step c) n=2 (i.e. two dimensional space), the results of the analysis are shown in a plane with points representing the images, the position of each image corresponding to said point in the 2-dimensional space, and a color representing the cluster or group it belongs to. In a second embodiment, and also considering that in said step c) n=2, the results of the analysis are shown in a grid, showing one image per grid point according to their position in the 2-dimensional space.

Moreover, in a third embodiment, when considering n=2 in step c), the method shows the results of the analysis in a plane with points representing the images, wherein a position of each image corresponds to said point in the 2-dimensional space, and a color representing a treatment performed on the eye corresponding each image, allowing to show a point of a yet untreated eye to decide a future treatment.

In an embodiment, the first nonlinear dimensionality reduction is performed with n being about 30 or above, the method, in this case further comprising executing a second nonlinear dimensionality reduction algorithm such as the IsoMap algorithm, the t-SNE algorithm, the Landmark IsoMap algorithm, the Kernel IsoMap algorithm, the Diffusion map algorithm, the multidimensional scaling algorithm, the Sammon mapping algorithm, (Deep) Autoencoders, Principal Component Analysis, Factor Analysis, Locally Linear Embedding, or Semidefinite embedding (SDE), also known as Maximum variance unfolding (MVU).

Other embodiments of the invention that are disclosed herein include software programs to perform the method embodiment steps and operations summarized above and disclosed in detail below. More particularly, a computer program product is one embodiment that has a computer-readable medium including computer program instructions encoded thereon that when executed on at least one processor in a computer system causes the processor to perform the operations indicated herein as embodiments of the invention.

Therefore, present invention provides a method for the detection of glaucoma and classification of angle types which improves the techniques known in the art in the sense that the images are automatically organized and makes diagnosis and objective comparison between several different cases easier. It can help both the doctor and the patient to decide which procedure to follow (especially if the map of the results was checked on what was done with the previous patients and sees where the new patient is on the map).

Present invention also minimizes the amount of information that must be put "by hand". The whole process works automatically, without any intervention of the user. The user should only interpret the results.

Moreover, the outputting of the result, i.e. a map where each point represents an image, also eases the glaucoma detection. This map can be used at the research level to classify objectively. At the clinical and educational level of the patient, it can be used to understand the patient's situation regarding a group of patients. In clinical management, the invention can be used to generate protocols and treat similar cases of similar forms. It could even be included in an OCT device to give warnings if the patient is at risk for some reason (which the technician or doctor may not have noticed if the patient did an OCT for other reasons).

BRIEF DESCRIPTION OF THE DRAWINGS

The previous and other advantages and features will be more fully understood from the following detailed description of embodiments, with reference to the attached figures, which must be considered in an illustrative and non-limiting manner, in which.

DETAILED DESCRIPTION OF PREFERRED EMBODIMENTS

Present invention provides a method for the unsupervised ordering (and optionally also classification) of OCT images. The input to the method is a database with anterior chamber OCT images (from various patients) and the output is a map in a two dimensional plane (and optionally a classification of such images in several groups that share common main features).

The method mainly consists of four main steps: preprocessing the images; performance of pair-wise distance measure between images; nonlinear dimensionality reduction; and visualization of results.

Figure 1:
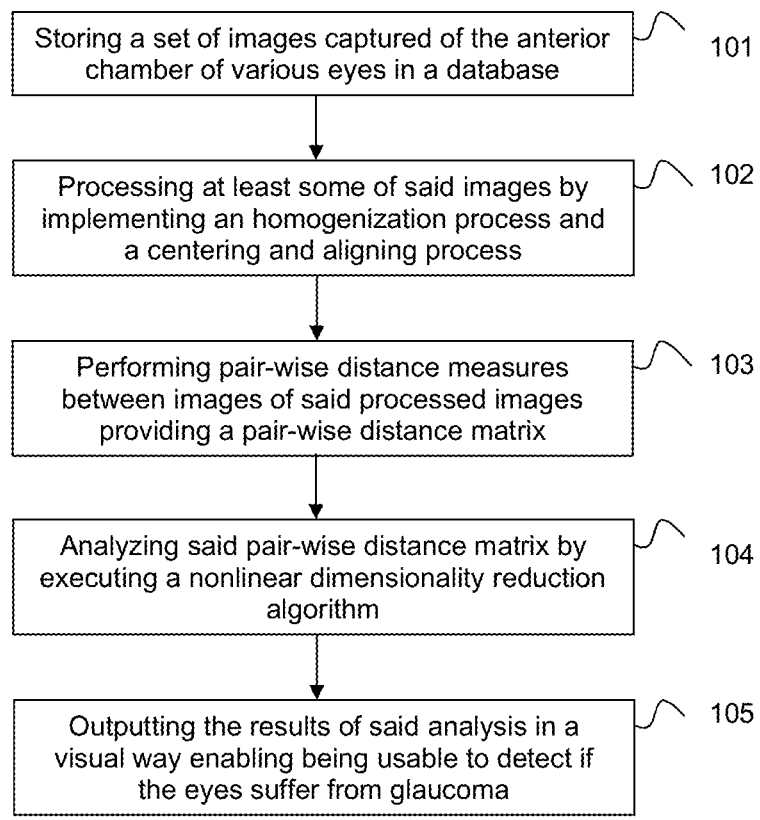
FIG. 1 illustrates a flow chart of an imaging processing method for glaucoma detection according to an embodiment of the present invention.

FIG. 1 shows an embodiment of the proposed method. According to this embodiment, once a set of images captured of the anterior chamber of the eyes of various patients are stored in a database, step 101, the stored images are processed, at step 102, by at least one processor of a computer system (not shown in the figures) by executing an homogenization process that adjusts an horizontal and a vertical spatial resolution of each image of the set to be the same, and by executing a centering and aligning process that computes statistical properties of the images, and uses said computed statistical properties to compute a centroid and a covariance matrix of each image. Following, at step 103, pair-wise distance measures between images of said processed images are performed providing a pair-wise distance matrix, and then, at step 104, said pair-wise distance matrix is analyzed by executing a (first) nonlinear dimensionality reduction algorithm (e.g. the IsoMap algorithm or the t-SNE algorithm, among others such as diffusion maps, Sammon mapping, etc.) that assigns a point in an n-dimensional space associated to each analyzed image. Typically a two dimensional space is used for visualization reasons, but the whole algorithm may work with any number of dimensions. Finally, at step 105, the results of said analysis are outputted in a visual way enabling being usable, for example by a doctor, to detect if said eyes suffers from angle closure glaucoma.

The outputting of the results may be done on a screen of said computer system, or alternatively in another computer system operatively connected to the computer system.

In an embodiment, the homogenization process performed at said step 102 may further convert the intensity of each pixel of each image to a double-precision floating-point number representation.

Besides, the processing of the images may further include the execution of a filtering process. This is done after the homogenization process. According to an embodiment of the proposed method, the filtering process first applies a two dimensional rectangular median filter to the image (for example, with 0.055-by-0.117 mm rectangle). Secondly, an anisotropic diffusion filter is applied; such filter is tuned to smooth the image preserving relevant edges. However, it should be noted that similar filtering techniques could be alternatively used.

Preferably, the set of statistical properties for the centering and aligning process, namely: S, X, Y, XX, YY, XY, are calculated such as: $S=\Sigma_{i,j}M(i,j)$, $X=\Sigma_{i,j}iM(i,j)$, $Y=\Sigma_{i,j}jM(i,j)$, $XX=\Sigma_{i,j}i^2M(i,j)$, $YY=\Sigma_{i,j}j^2M(i,j)$ and $XY=\Sigma_{i,j}ijM(i,j)$, where M(i,j) is the (gray) value of the image on the pixel that is i pixels down from the top edge and j pixels right from the left edge. With those properties the centroid of the image whose coordinates are, $$(i, j) = \left(\frac{Y}{S}, \frac{X}{S}\right)$$

and the covariance matrix $$COV = \begin{pmatrix} YY/S - Y^2/S^2 & XY/S - (X/S)(Y/S) \\ XY/S - (X/S)(Y/S) & XX/S - X^2/S^2 \end{pmatrix}$$

are calculated.

In addition, $v_1$ is defined to be the eigenvector of the covariance matrix corresponding to the largest eigenvalue. With those parameters a new image ($M_c$) is created which is twice as large as M, where M is copied such that centroid of M coincides with the center of $M_c$ and $v_1$ is aligned with the horizontal direction.

After this step a resolution reduction may be done to boost the performance of the method.

The pair-wise distance matrix obtained in said step 103, which can be represented as (D(l,m)), whose entries are the pair-wise distances between images l and m (l and m varying between 1 and the number of images in the set), can be obtained using the Hellinger distance, although similar results can be obtained using other distance definitions such as the Mahalanobis distance, the Jensen-Shannon divergence, $L_p$ Minkowski family $$\left(D(l, m) = d_{Lp}(M_{cl}, M_{cm}) = \sqrt[p]{\sum_{i,j}|M_{cl} - M_{cm}|^p}\right)$$

with p chosen between 0 and infinity, etc. So, the following equation can be used for that purpose:

$$D(l, m) = d_H(M_{cl}, M_{cm}) = \sqrt{2\sum_{i,j}\left(\sqrt{\frac{M_{cl}}{S_l}} - \sqrt{\frac{M_{cm}}{S_m}}\right)^2}$$

Regarding the analysis step (step 104), according to an embodiment, this step may further include the execution of a community detection algorithm such as InfoMap to identify clusters or groups of similar images. To do so, an adjacency matrix is defined using the pair-wise distance matrix. This might be done simply using a threshold or more sophisticatedly using a decreasing monotonous function entry-by-entry to the distance matrix to produce the adjacency matrix. As a result of the algorithm the database is divided into a set of groups such that images within the same group are similar, i.e., they share common features.

In an embodiment, a second nonlinear dimensionality reduction algorithm can be executed if in said step 104 the first nonlinear dimensionality reduction algorithm is performed with a big n (about 30 or more).

Figure 2:
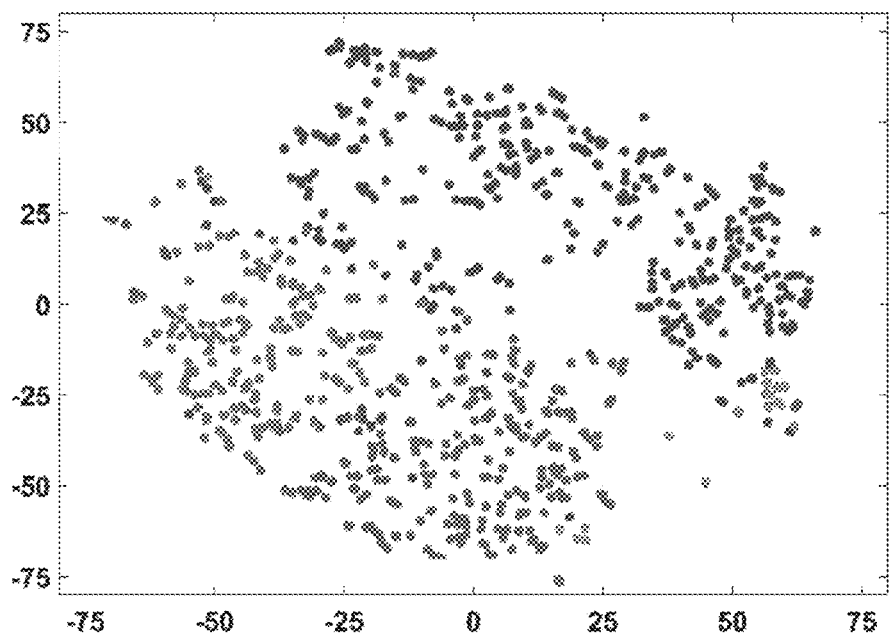
FIGS. 2 and 3 depict two examples of how the results can be outputted, full map visualization and image map visualization, respectively.

Referring now to FIG. 2, therein it is illustrated an embodiment of how the results can be outputted. In this visualization, a plane with points representing the images, the position of each image corresponds to its mapped coordinates, and a color representing the group it belongs to is shown. It also allows an expert to inspect the images corresponding to each group (or some of them) to label the groups in a meaningful manner.

Figure 3:
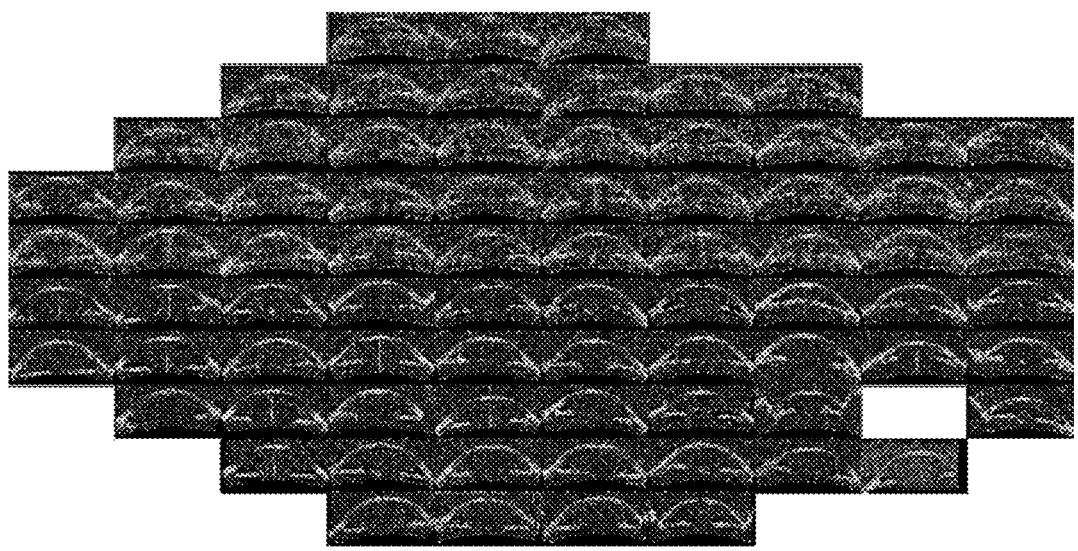

FIG. 3 illustrates another embodiment of how the results can be outputted. In this visualization, a regular grid in the mapped coordinate's space is constructed and one image per grid point is shown according to their position in the mapped coordinates. The result is a big image consisting of many small OCT images.

Although the above embodiments have been described by considering that the images are OCT images, present invention can equally work with other type of images of the anterior chamber, for instance images obtained by ultrasound techniques, or a Scheimpflug camera for ophthalmology.

The proposed invention may be implemented in hardware, software, firmware, or any combination thereof. If implemented in software, the functions may be stored on or encoded as one or more instructions or code on a computer-readable medium.

Computer-readable media includes computer storage media. Storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. Any processor and the storage medium may reside in an ASIC. The ASIC may reside in a user device. In the alternative, the processor and the storage medium may reside as discrete components in a user device.

As used herein, computer program products comprising computer-readable media including all forms of computer-readable medium except, to the extent that such media is deemed to be non-statutory, transitory propagating signals.

The scope of the present invention is defined in the following set of claims.

What is claimed is:

1. Image processing method for glaucoma detection, the method comprising:
   storing in a database a set of images captured of the anterior chamber of various eyes from various patients; and
   using a processor performing the following steps:
   a) processing at least some of said stored images by implementing:
      an homogenization process that adjusts an horizontal and a vertical spatial resolution of each image of the set to be the same, and
      a centering and aligning process that computes statistical properties of the images, and uses said computed statistical properties to compute a centroid and a covariance matrix of each image;
   b) performing pair-wise distance measures between images of said processed images providing a pair-wise distance matrix;
   c) analyzing said pair-wise distance matrix by executing a first nonlinear dimensionality reduction algorithm that assigns a point in an n-dimensional space associated to each analyzed image; and
   d) outputting the results of said analysis in a visual way enabling being usable to detect if said eyes suffer from glaucoma.

2. The method of claim 1, wherein in said step a) all the stored images are processed.

3. The method of claim 1, wherein said set of images of the anterior chamber being optical coherence tomography (OCT) images.

4. The method of claim 1, wherein said homogenization process further converts the intensity of each pixel of each image to a double-precision floating-point number representation.

5. The method of claim 1, wherein said step a) further comprises implementing a filtering process comprising at least one of the following filtering techniques after the homogenization process: Rectangular median filter, Anisotropic diffusion filter, Bilateral filter, Guide filter, Total variation denoising, Convolutional (Gaussian) filter, and/or Non-local means filtering.

6. The method of claim 1, wherein the first nonlinear dimensionality reduction algorithm comprises an IsoMap algorithm, a t-SNE algorithm, a Landmark IsoMap algorithm, a Kernel IsoMap algorithm, a Diffusion map algorithm, a multidimensional scaling algorithm, or a Sammon mapping algorithm.

7. The method of claim 1, wherein said step c) further comprises executing a community detection algorithm to an adjacency matrix derived from the pair-wise distance matrix to identify clusters or groups of similar images.

8. The method of claim 7, wherein the community detection algorithm comprises an InfoMap algorithm, a DBSCAN algorithm, a Leading eigenvector algorithm, a Fast Greedy Modularity Maximization algorithm, a Walktrap algorithm, a Label Propagation algorithm, a Spinglass algorithm, or an Edge Betweeness algorithm.

9. The method of claim 7, wherein in said step c) n=2 and said step d) comprises showing the results of the analysis in a plane with points representing the images, wherein a position of each image corresponds to said point in the 2-dimensional space, and a color representing the cluster or group it belongs to.

10. The method of claim 1, wherein in said step c) n=2 and said step d) comprises showing the results of the analysis in a grid, showing one image per grid point according to their position in the 2-dimensional space.

11. The method of claim 1, wherein in said step b) the pair-wise distance measure comprises a Hellinger distance, an Euclidean distance, a distance from the $L_p$ Minkowski family with any p from 0 to infinity, a Jensen-Shannon divergence, a Mahalanobis Distance, a Chord Distance, a Sayood distance, or an Earth Mover's Distance also known as Wasserstein metric.

12. The method of claim 1, wherein in said step c) the first nonlinear dimensionality reduction is performed with n being at least 30, the method further comprising executing a second nonlinear dimensionality reduction algorithm, said second nonlinear dimensionality algorithm comprising an IsoMap algorithm, a t-SNE algorithm, a Landmark IsoMap algorithm, a Kernel IsoMap algorithm, a Diffusion map algorithm, a multidimensional scaling algorithm, a Sammon mapping algorithm, (Deep) Autoencoders, Principal Component Analysis, Factor Analysis, Locally Linear Embedding, or Semidefinite embedding (SDE), also known as Maximum variance unfolding (MVU).

13. The method of claim 7, wherein in said step c) n=2 and said step d) comprises showing the results of the analysis in a plane with points representing the images, wherein a position of each image corresponds to said point in the 2-dimensional space, and a color representing a treatment performed on the eye corresponding each image, allowing to show a point of a yet untreated eye to decide a future treatment.

14. A non-transitory computer program product comprising code instructions that when executed in at least one processor of a computer system implement a method performing the following steps:
   a) processing some images captured of the anterior chamber of various eyes from various patients by implementing:
      an homogenization process that adjusts an horizontal and a vertical spatial resolution of each image of the set to be the same, and
      a centering and aligning process that computes statistical properties of the images, and uses said computed statistical properties to compute a centroid and a covariance matrix of each image;
   b) performing pair-wise distance measures between images of said processed images providing a pair-wise distance matrix;
   c) analyzing said pair-wise distance matrix by executing a first nonlinear dimensionality reduction algorithm that assigns a point in an n-dimensional space associated to each analyzed image; and
   d) outputting the results of said analysis in a visual way enabling being usable to detect if said eyes suffer from glaucoma.

15. The method of claim 7, wherein in said step c) n=2 and said step d) comprises showing the results of the analysis in a grid, showing one image per grid point according to their position in the 2-dimensional space.

16. The method of claim 6, wherein in said step c) the first nonlinear dimensionality reduction is performed with n being at least 30, the method further comprising executing a second nonlinear dimensionality reduction algorithm, said second nonlinear dimensionality algorithm comprising an IsoMap algorithm, a t-SNE algorithm, a Landmark IsoMap algorithm, a Kernel IsoMap algorithm, a Diffusion map algorithm, a multidimensional scaling algorithm, a Sammon mapping algorithm, (Deep) Autoencoders, Principal Component Analysis, Factor Analysis, Locally Linear Embedding, or Semidefinite embedding (SDE), also known as Maximum variance unfolding (MVU).

* * * * *